United States Patent
Ruff et al.

(10) Patent No.: US 11,793,486 B2
(45) Date of Patent: Oct. 24, 2023

(54) ULTRASOUND SYSTEM PROBE HOLDER

(71) Applicant: General Electric Company, Schenectady, NY (US)

(72) Inventors: Christian Ruff, Zipf (AT); Gerhard Hattinger, Zipf (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1351 days.

(21) Appl. No.: 16/106,565

(22) Filed: Aug. 21, 2018

(65) Prior Publication Data

US 2020/0060647 A1 Feb. 27, 2020

(51) Int. Cl.
*A61B 8/00* (2006.01)

(52) U.S. Cl.
CPC .............. *A61B 8/44* (2013.01); *A61B 8/4405* (2013.01)

(58) Field of Classification Search
None
See application file for complete search history.

(56) References Cited

U.S. PATENT DOCUMENTS

| | | | |
|---|---|---|---|
| 5,615,678 A * | 4/1997 | Kirkham | A61B 8/44 600/459 |
| 5,673,696 A | 10/1997 | Bidwell et al. | |
| 6,629,927 B1 | 10/2003 | Mesaros et al. | |
| D901,019 S * | 11/2020 | Nally | D24/186 |
| 2003/0236463 A1 * | 12/2003 | Mesaros | A61B 8/00 600/459 |
| 2008/0255455 A1 * | 10/2008 | Sokulin | A61B 8/4209 600/459 |
| 2010/0324444 A1 | 12/2010 | Mollere | |

(Continued)

FOREIGN PATENT DOCUMENTS

| CN | 101278842 A | 10/2008 |
|---|---|---|
| CN | 105796127 A | 7/2016 |

(Continued)

OTHER PUBLICATIONS

Medray Imaging, "Carestream Touch Prime Ultrasound System," (Sep. 6, 2016), retrieved from <https://www.youtube.com/watch?v=-9-OGStO4mM> on Jan. 3, 2023. (Year: 2016).*

(Continued)

*Primary Examiner* — Joel Lamprecht
*Assistant Examiner* — Ashish S Jasani
(74) *Attorney, Agent, or Firm* — McAndrews, Held & Malloy, Ltd.; Jacob Groethe; David Bates

(57) ABSTRACT

A panel may include an inner edge, an outer edge opposite the inner edge, and a probe holder apparatus formed in the panel between the inner edge and the outer edge. The probe holder apparatus may have a generally rectangular shape comprising a front outer corner, a rear outer corner, a front inner corner, and a rear inner corner. The probe holder apparatus may include a slot, at least one surface within the probe holder apparatus, and a cable guide. The slot may extend from a center of the probe holder apparatus through the outer edge of the panel. The at least one surface may be configured to receive a body of an ultrasound probe. The at least one surface may have a diameter. The cable guide may include an inclined surface protruding from the front outer corner of the probe holder apparatus.

17 Claims, 6 Drawing Sheets

(56) References Cited

U.S. PATENT DOCUMENTS

| | | | |
|---|---|---|---|
| 2014/0257145 A1 | 9/2014 | Emery | |
| 2014/0259604 A1* | 9/2014 | Romano | A61B 8/4422 29/281.1 |
| 2017/0281126 A1* | 10/2017 | Meurer | A61B 8/4405 |

FOREIGN PATENT DOCUMENTS

| | | | | |
|---|---|---|---|---|
| JP | 7178097 A | | 7/1995 | |
| JP | 2011036302 A | | 2/2011 | |
| JP | 2012143330 A | | 8/2012 | |
| JP | 06166815 B1 | | 6/2017 | |
| JP | 2019126454 A | * | 8/2019 | A61B 8/4209 |
| WO | 2003099127 A1 | | 12/2003 | |
| WO | 2014207593 A1 | | 12/2014 | |
| WO | 2015059597 A1 | | 4/2015 | |

OTHER PUBLICATIONS

General Electric Co., "LOGIQ S7 Expert/Pro User Guide", Technical Publications, Direction 5453159-100, Rev. 2, Aug. 12, 2012, 201 pages.

\* cited by examiner

ULTRASOUND SYSTEM PROBE HOLDER

FIELD

Certain embodiments relate to ultrasound systems. More specifically, certain embodiments relate to a panel having one or more probe holders for holding an ultrasound transducer of an ultrasound system.

BACKGROUND

Ultrasound imaging is a medical imaging technique for imaging organs and soft tissues in a human body. Ultrasound imaging is typically performed using an ultrasound machine. Ultrasound machines commonly include one or more transducers (also referred to as ultrasound probes), a display, and user controls. Some ultrasound machines include accessories for holding one or more ultrasound probes when the probes are not being used. Conventional probe holders are generally circular openings typically positioned at outside edges of side panels adjacent the user control panel of the ultrasound machine. A slot extending between the outer edge of the side panel and the generally circular opening is centered with the generally circular opening and used to insert the ultrasound probe and probe cord into the generally circular opening and remove the ultrasound probe and probe cord from the generally circular opening. More specifically, a user may grasp a body of an ultrasound probe connected to the ultrasound system by a probe cord, move the probe cord through the slot, and place the ultrasound probe on or within the generally circular opening. The diameter of the generally circular opening may be sized to be smaller than the largest diameter of a particular or smallest ultrasound probe such that the probe is secured above and/or partially within the generally circular opening.

With most conventional probe holders, the user completely removes the ultrasound probe and probe cable from the holder prior to performing an ultrasound scan. More specifically, the user may grasp and lift the probe from the generally circular opening of the probe holder and guide the probe cord out of the slot of the probe holder in order to use the ultrasound probe. The process of removing the ultrasound probe and probe cord from the probe holder prior to use and subsequently replacing the ultrasound probe and probe cord into the probe holder after use are additional steps that add to the amount of time needed to perform an ultrasound scan. Moreover, the use of the ultrasound probe once removed from a conventional probe holder may provide stress to a hand of the sonographer due to the weight of the cable connecting the ultrasound probe to the ultrasound machine. In probe holders designed to retain the probe cable during use, the ultrasound probe may be difficult to maneuver because the probe cable does not easily slide within the probe holder. Furthermore, the quality of the fit provided by a particular probe holder may vary depending on the type of ultrasound probe being used.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

An ultrasound system probe holder apparatus having at least one cable guide, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
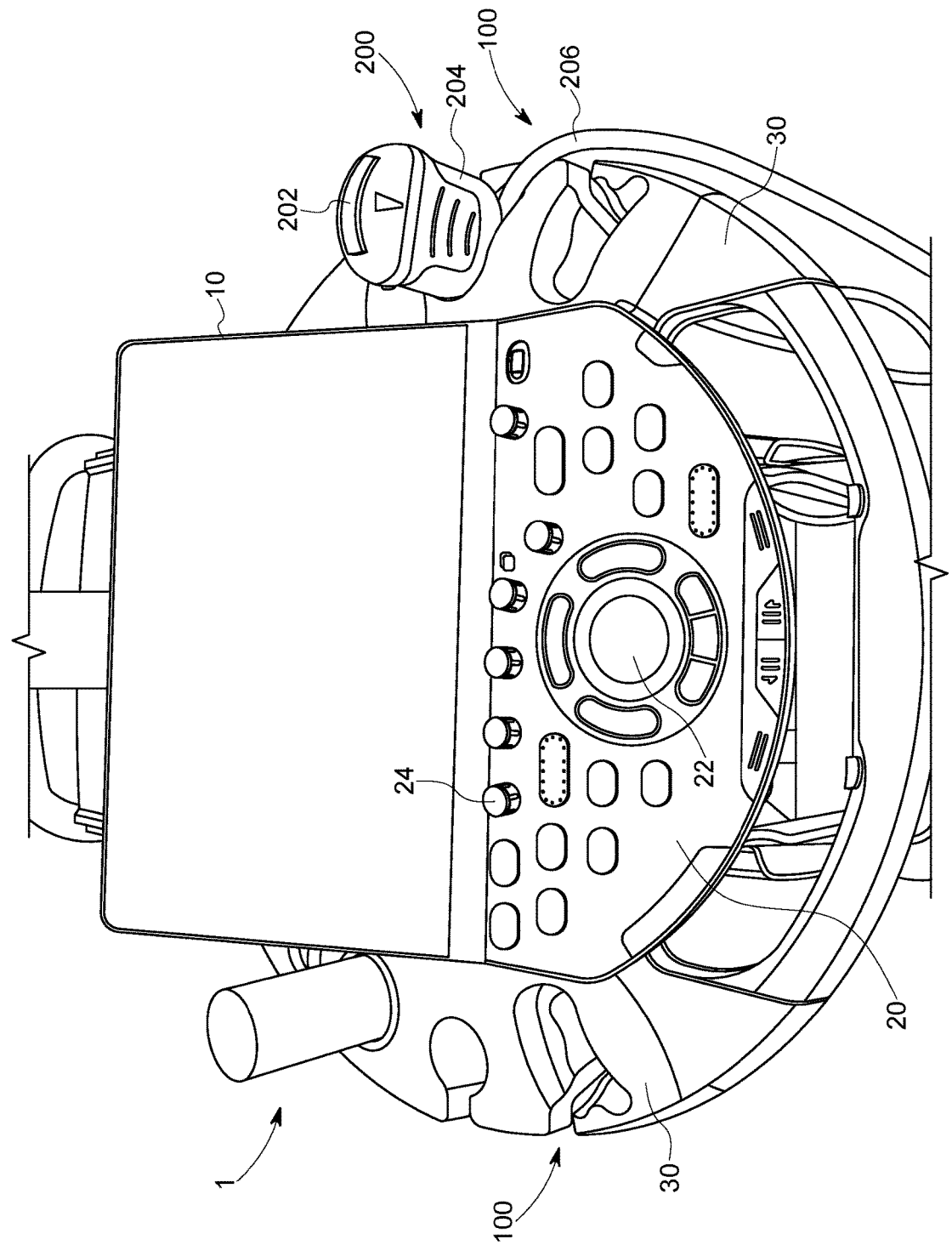
FIG. 1 illustrates a front perspective view of an exemplary ultrasound machine having probe holder apparatuses, in accordance with various embodiments.

Certain embodiments may be found in an ultrasound system probe holder apparatus. The probe holder apparatus may allow use of the ultrasound probe with the probe cord guided through a cable guide integrated into the probe holder to save time by not having to remove the probe cord from the probe holder apparatus and to alleviate stress from a hand of a sonographer by having the probe cord rest within the cable guide during use of the ultrasound probe. In various embodiments, the probe holder apparatus may be configured with probe cord retaining properties for preventing unintentional removal of the probe cord from the probe holder apparatus. In an exemplary embodiment, the probe holder apparatus may include a plurality of tiered surfaces configured to enhance the fit of different ultrasound probe types with the probe holder apparatus.

The foregoing summary, as well as the following detailed description of certain embodiments will be better understood when read in conjunction with the appended drawings. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present disclosure. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

FIG. 1 illustrates a front perspective view of an exemplary ultrasound machine 1 having probe holder apparatuses 100, in accordance with various embodiments. Referring to FIG. 1, the ultrasound machine 1 comprises a display system 10, control panel 20, one or more side panels 30, and an ultrasound probe 200.

The display system 10 may be any device capable of communicating visual information to a user. For example, a display system 10 may include a liquid crystal display, a light emitting diode display, and/or any suitable display or displays. The display system 10 can be operable to display information from one or more processors or memories of the ultrasound machine 1, such as medical images acquired by the ultrasound probe 200 or any suitable information. In various embodiments, the display system 10 may be a touchscreen display configured to receive user directives via touch input.

The control panel 20 may include user input device(s) 22, 24 capable of communicating information from a user and/or at the direction of the user to one or more processors of the ultrasound machine 1, for example. The user input devices 22, 24 may include a trackball 22, rotary encoders 24, button(s), a mousing device, keyboard, camera, voice recognition microphone, and/or any other device capable of receiving a user directive. In certain embodiments, one or more of the user input devices may be integrated into other components, such as the display system 10, for example. As an example, a user input device may include a touchscreen display.

The ultrasound probe 200 may comprise a transducer head 202, a probe body 204, and a probe cord 206. The transducer head 202 may include a two dimensional (2D) array of piezoelectric elements. A group of transmit transducer elements and a group of receive transducer elements that normally constitute the same elements may be disposed within the transducer head 202 and/or probe body 204. In certain embodiment, the ultrasound probe 200 may be operable to acquire ultrasound image data. The ultrasound image data may be sent from the ultrasound probe 200 to one or more processors of the ultrasound machine 1 via probe cord 206. Control signals may be provided by the user input devices 22, 24 and/or the one or more processors to the ultrasound probe 200 via the probe cord 206. The probe body 204 may be a housing configured to be held by a user performing an ultrasound scan or otherwise manipulating the ultrasound probe 200. The ultrasound probe 200 may be placed in a probe holder apparatus 100 of the ultrasound machine 1 when not in use.

The one or more side panels 30 may include probe holder apparatuses 100 and any suitable fixtures for storing ultrasound components and/or accessories. The probe holder apparatuses 100 may be configured to store an ultrasound probe 200 when not in use. As described below, the probe holder apparatuses 100 may be configured to guide and alleviate the weight of the probe cord 206 when the ultrasound probe 200 is in use or is otherwise being manipulated by a user.

Figure 2:
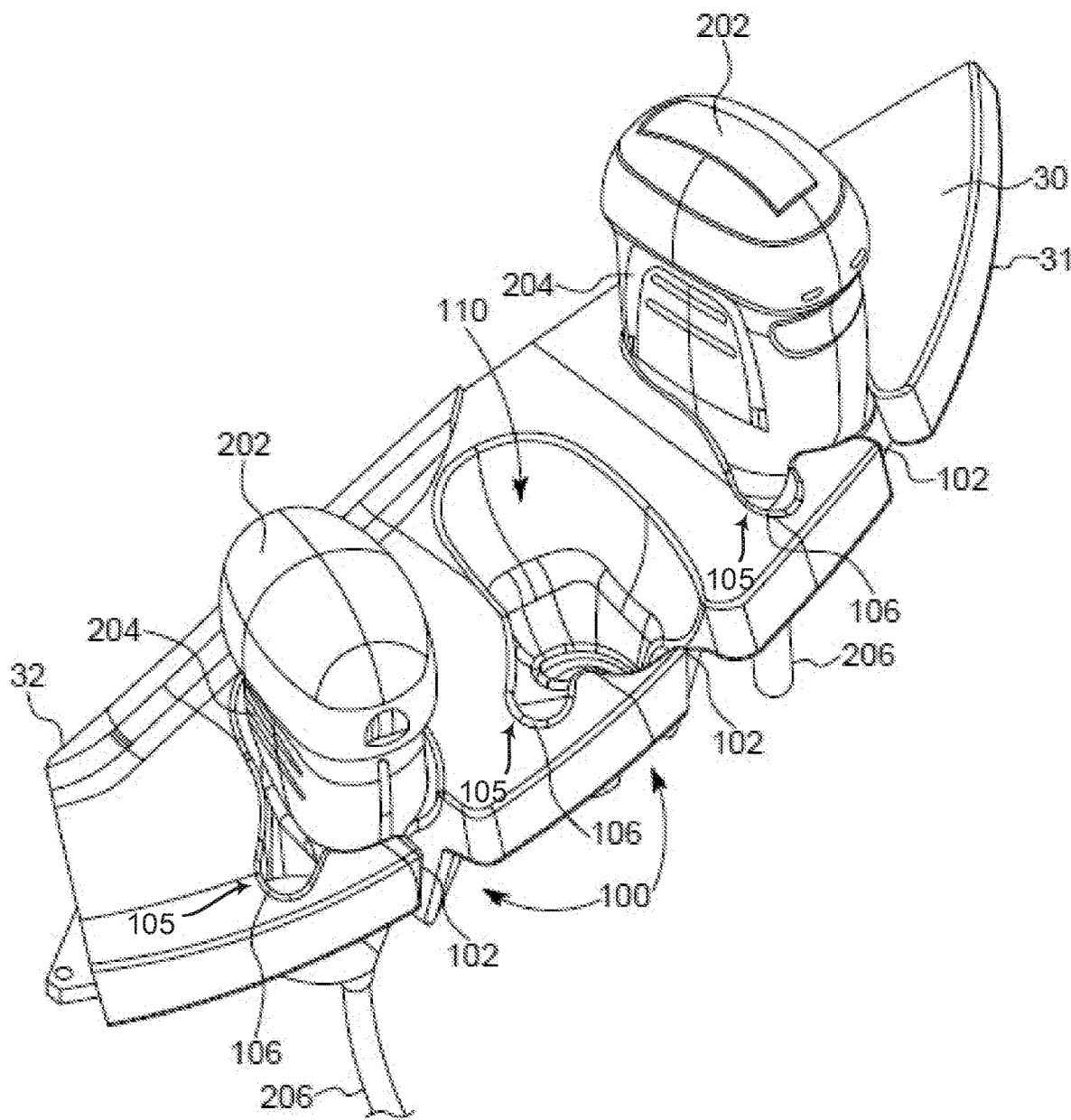
FIG. 2 illustrates a side perspective view of an exemplary panel of an ultrasound machine having ultrasound system probe holder apparatuses that include at least one cable guide, in accordance with various embodiments.

FIG. 2 illustrates a side perspective view of an exemplary panel 30 of an ultrasound machine 1 having ultrasound system probe holder apparatuses 100 that include at least one cable guide 106, in accordance with various embodiments. Referring to FIG. 2, an ultrasound machine panel 30 having probe holder apparatuses 100 configured to hold ultrasound probes 200 is shown.

The ultrasound machine panel 30 includes an outer edge 31 and an inner edge 32. The inner edge 32 may be configured to attach to the control panel 30, display system 10, and/or may form a portion of a portable cart of the ultrasound machine 1. The outer edge 31 may include slots 102 of the probe holder apparatuses 100.

The probe holder apparatuses 100 may include the slot 102, a cable guide 106, and one or more surfaces 110 formed within the probe holder apparatus 100. The probe holder apparatuses 100 may be generally rectangular with rounded corners, oval, or any suitable shape. The probe holder apparatuses 100 may include a rear, inner corner portion generally corresponding toward the rear and inner edge 32 of the side panel 30 of the ultrasound machine 1. The probe holder apparatuses 100 may include a front, inner corner portion generally corresponding toward the front and inner edge 32 of the side panel 30 of the ultrasound machine 1. The probe holder apparatuses 100 may include a rear, outer corner portion generally corresponding toward the rear and outer edge 31 of the side panel 30 of the ultrasound machine 1. The probe holder apparatuses 100 may include a front, outer corner portion generally corresponding toward the front and outer edge 31 of the side panel 30 of the ultrasound machine 1. The front, outer corner portion may include a bump-out projection 105 defining the cable guide 106. The cable guide 106 may be a ramped surface extending from within the probe holder apparatus 100 upward and outward into the bump-out projection 105 at the front, outer corner portion of the probe holder apparatus 100. The slot 102 may extend at an angle from the center of the probe holder apparatus 100 through the rear, outer corner portion of the probe holder apparatus 100 and through the outer edge 31 of the panel 30.

The ultrasound probe 200 may comprise a transducer head 202, a probe body 204, and a probe cord 206. The transducer head 202 may be configured to transmit and receive ultrasound signals. The probe body 204 may be a housing configured to be held by a user performing an ultrasound scan or otherwise manipulating the ultrasound probe 200. The probe cord 206 may be configured to transmit ultrasound control signals from the ultrasound machine 1 to the ultrasound probe 200 and to transmit ultrasound image data from the ultrasound probe 200 to the ultrasound machine 1.

In various embodiments, the ultrasound probe 200 may be inserted into the probe holder apparatus 100 by: (1) positioning the transducer head 202 and probe body 204 upright and above the probe holder apparatus 100 outside the outer edge 31 of the side panel 30, (2) moving the ultrasound probe 200 toward the center of the probe holder apparatus 100 while manipulating the probe cord 206 through the slot 102 extending from the outer edge 31 of the side panel 30 to the center of the probe holder apparatus 100, and (3) lowering the ultrasound probe 200 to rest the probe body 204 on the appropriately-sized surface 110 within the probe holder apparatus 100. As described in more detail below, the one or more surfaces 110 may include tiered surfaces 112, 114, 116 each sized to receive a different ultrasound probe size. For example, each of the surfaces 110 may be compatible with different types of ultrasound probes 200, such as convex, micro-convex, phased array, linear, t-type linear, biplanar, endocavitary, intrarectal, and/or any suitable ultrasound probe 200.

In certain embodiments, the ultrasound probe 200 may be used with the probe holder apparatus 100 by: (1) lifting the ultrasound probe 200 from the surface 110 within the probe holder apparatus 100, (2) guiding the probe cord 206 of the ultrasound probe 200 into a notched opening 104 and onto the ramped surface of the cable guide 106 of the probe holder apparatus 100, and (3) manipulating the ultrasound probe 200 to perform an ultrasound scan, the probe cord 206 of the ultrasound probe 200 sliding and/or resting on the ramped surface of the cable guide 106 as the probe 200 is manipulated to perform the scan.

The side panel 30, probe holder apparatuses 100, and ultrasound probes 200 illustrated in FIG. 2 shares various characteristics with the side panels 30, probe holder apparatuses 100, and ultrasound probe 200 illustrated in FIG. 1 as described above.

Figure 3:
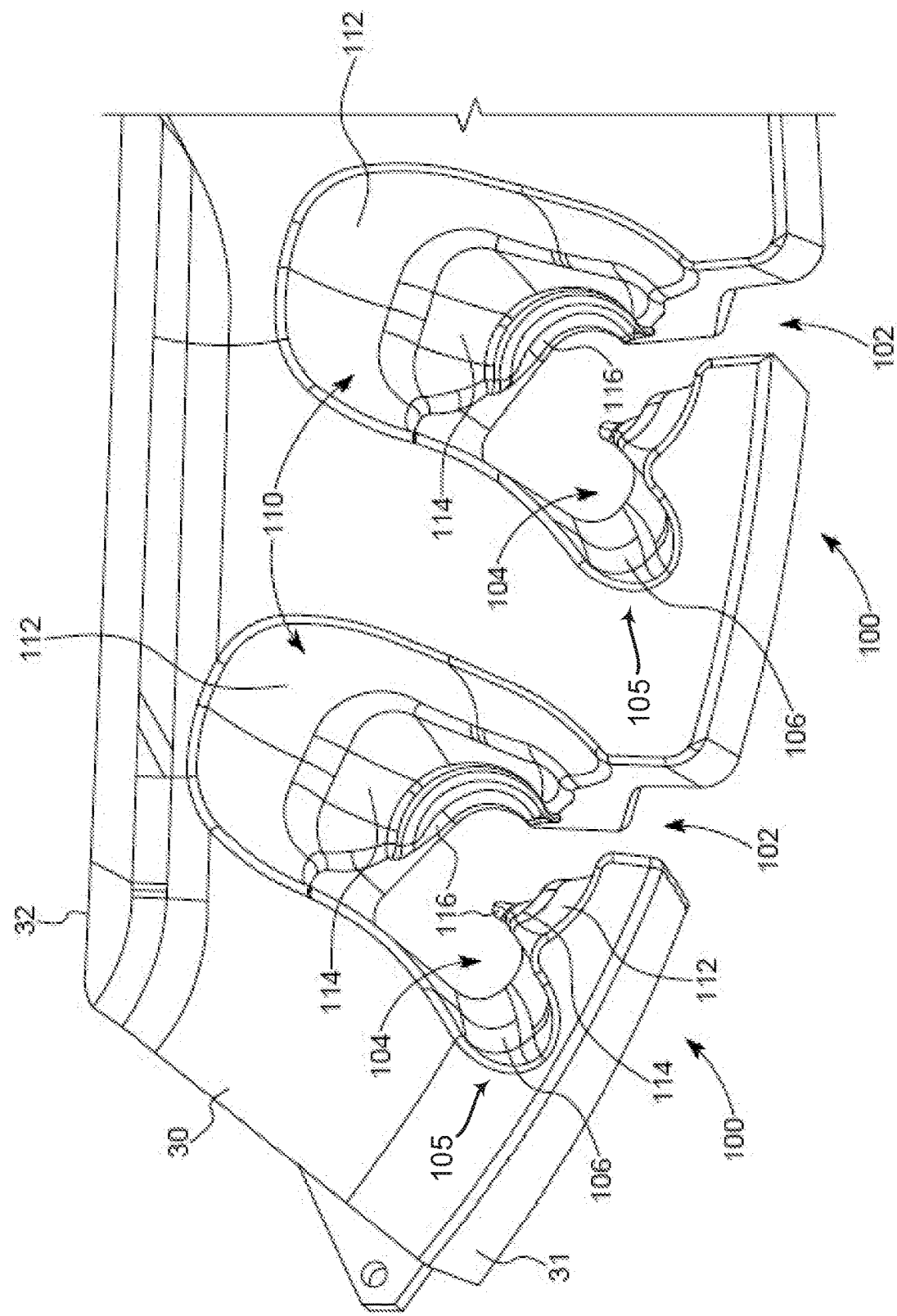
FIG. 3 illustrates a side perspective view of a portion of an exemplary panel of an ultrasound machine having ultrasound system probe holder apparatuses that include at least one cable guide, in accordance with various embodiments.
Figure 4:
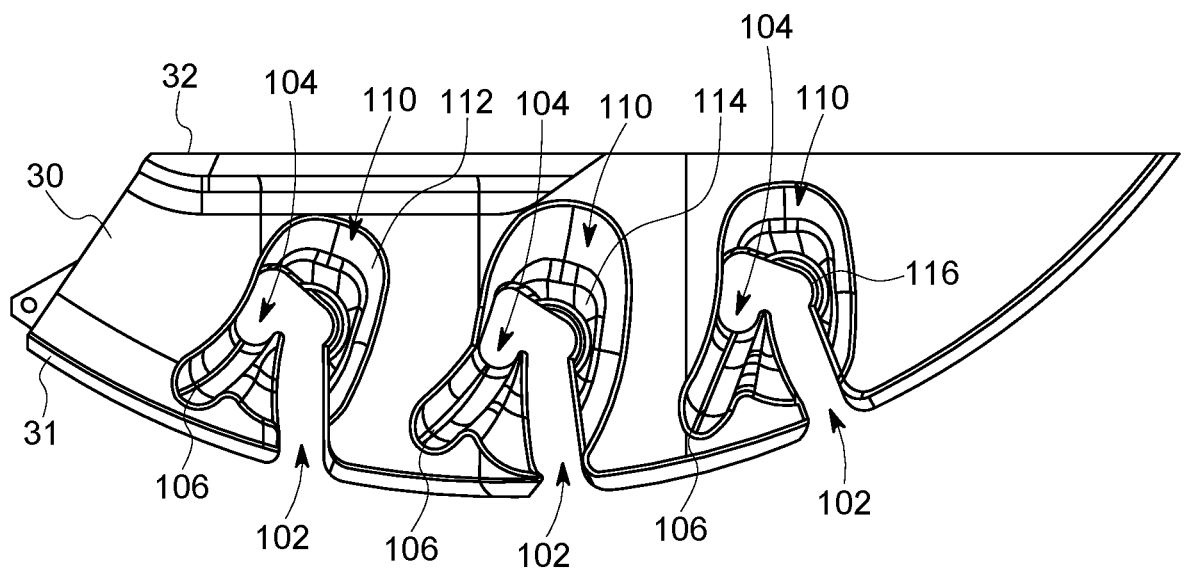
FIG. 4 illustrates a top elevation view of an exemplary panel of an ultrasound machine having ultrasound system probe holder apparatuses that include at least one cable guide, in accordance with various embodiments.
Figure 5:
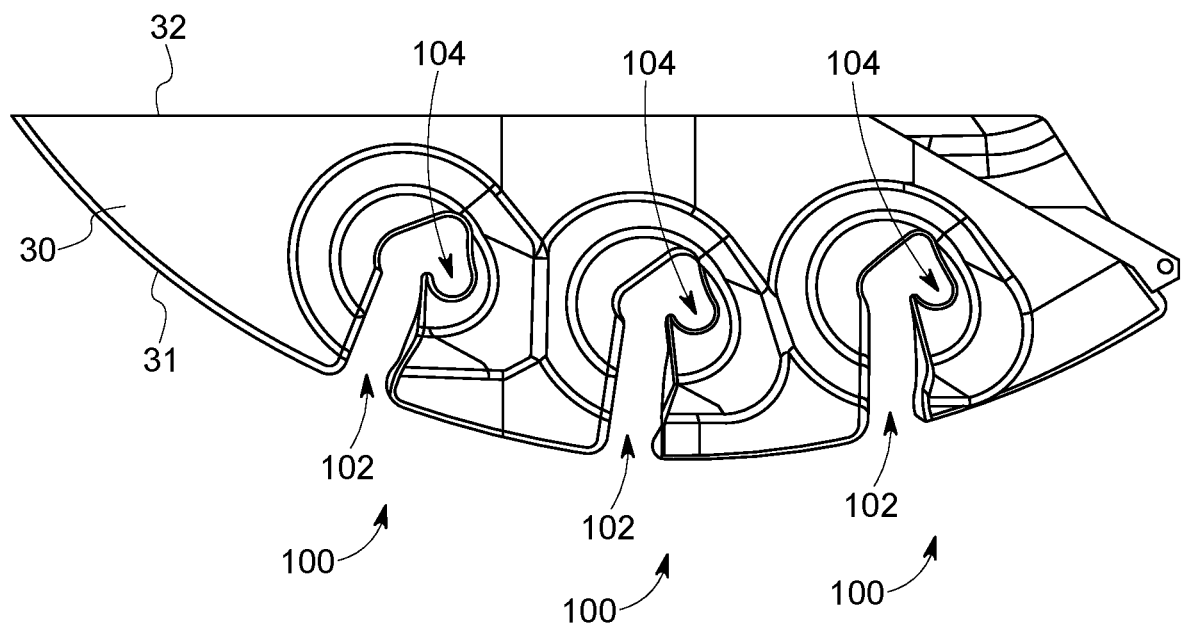
FIG. 5 illustrates a bottom elevation view of an exemplary panel of an ultrasound machine having ultrasound system probe holder apparatuses that include at least one cable guide, in accordance with various embodiments.

FIG. 3 illustrates a side perspective view of a portion of an exemplary panel 30 of an ultrasound machine 1 having ultrasound system probe holder apparatuses 100 that include at least one cable guide 106, in accordance with various embodiments. FIG. 4 illustrates a top elevation view of an exemplary panel 30 of an ultrasound machine 1 having ultrasound system probe holder apparatuses 100 that include at least one cable guide 106, in accordance with various embodiments. FIG. 5 illustrates a bottom elevation view of an exemplary panel 30 of an ultrasound machine 1 having ultrasound system probe holder apparatuses 100 that include at least one cable guide 106, in accordance with various embodiments. Referring to FIGS. 3-5, a panel 30 having probe holder apparatuses 100 is shown. The panel 30 includes an outer edge 31 and an inner edge 32. The inner edge 32 may be configured to attach to the control panel 30, display system 10, and/or may form a portion of a portable cart of the ultrasound machine 1, among other things. The outer edge 31 may include slots 102 of the probe holder apparatuses 100.

The probe holder apparatuses 100 may include the slot 102, a notched opening 104, a cable guide 106, and one or more surfaces 110 formed within the probe holder apparatus 100. The slot 102 may extend at an angle from the center of the probe holder apparatus 100 through the rear, outer corner portion of the probe holder apparatus 100 and through the outer edge 31 of the panel 30. The angle of the slot 102 from the center of the probe holder apparatus 100 to a corner of the probe holder apparatus 100 may assist in preventing a probe cable 206 of an ultrasound probe 200 from inadvertently moving out of the probe holder apparatus 100 during use of the ultrasound probe 200.

The notched opening 104 may further assist in preventing the probe cable 206 from in advertently moving out of the probe holder apparatus 100. The notched opening 104 may be a generally L-shaped opening extending between the cable guide 106 and the slot 102. The notched opening 104 may be contiguous with the slot 102. The corner formed by the notched opening 104 between a portion where the notched opening 104 meets the cable guide 106 and a portion where the notched opening 104 meets the slot 102 biases a probe cable 206 slidably positioned in the cable guide 106 to remain within the probe holder apparatus 100 during use of the ultrasound probe 200.

The cable guide 106 may be a ramped surface extending from within the probe holder apparatus 100 adjacent the notched opening 104 upward and outward into a bump-out projection 105 at the front, outer corner portion of the probe holder apparatus 100. The cable guide 106 reduces the amount of friction between a probe cable 206 and the probe holder apparatus 100 while guiding the probe cable 206 as the probe cable 206 is pulled through the probe holder apparatus 100 during use of the ultrasound probe 200.

The one or more surfaces 110 formed within the probe holder apparatus 100 may be configured to receive and hold an ultrasound probe 200. The one or more surfaces 110 may include a plurality of parallel, tiered surfaces 112, 114, 116 that decrease in diameter from a top of the probe holder apparatus 100 to a bottom of the probe holder apparatus 100. For example, a first surface 112 may be located nearest a top of the probe holder apparatus 100 and may have a widest diameter. A second surface 116 may be located nearest a bottom of the probe holder apparatus 100 and may have a narrowest diameter. One or more intermediary surfaces 114 may be positioned between the first surface 112 and the second surface 116 and may have decreasing diameters moving from first surface 112 toward the second surface 116. Each of the tiered surfaces 112, 114, 116 may be sized to fit different sized ultrasound probes 200 to provide a universal probe holder apparatus 100 capable of holding any suitable ultrasound probe 200. In various embodiments, each of the parallel, tiered surfaces 112, 114, 116 may be generally in a same plane but may be non-continuous, as shown in FIG. 3. For example, each of the parallel, tiered surfaces 112, 114, 116 may include a first portion that extends at least partially between a first side of the cable guide 106 and a first side of the slot 102 and a second portion that extends at least partially between a second side of the cable guide 106 and a second side of the slot 102. The term diameter may refer to the distance between the first portion and the second portion of each of the tiered surfaces 112, 114, 116.

The side panels 30 and probe holder apparatuses 100 illustrated in FIGS. 3-5 share various characteristics with the side panels 30 and probe holder apparatuses 100 illustrated in FIGS. 1 and 2 as described above.

Figure 6:
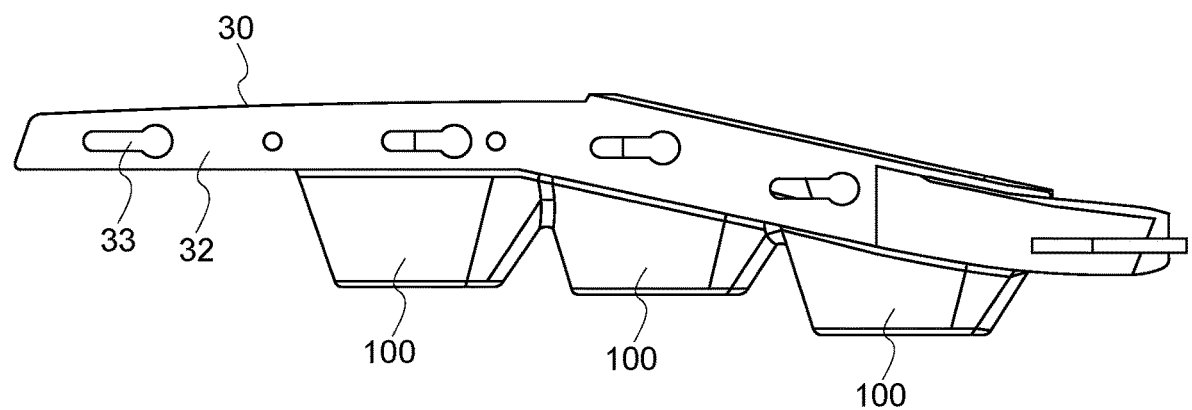
FIG. 6 illustrates an inner side elevation view of an exemplary panel of an ultrasound machine having ultrasound system probe holder apparatuses that include at least one cable guide, in accordance with various embodiments.

FIG. 6 illustrates an inner side elevation view of an exemplary panel 30 of an ultrasound machine having ultrasound system probe holder apparatuses 100 that include at least one cable guide 106, in accordance with various embodiments. Referring to FIG. 6, the panel 30 comprises an outer edge 31, an inner edge 32, and probe holder apparatuses 100 formed between the outer 31 and inner 32 edges. The inner edge 32 may include one or more attachment devices 33 configured to attach the inner edge 32 to the control panel 30, display system 10, and/or a portion of a portable cart of the ultrasound machine 1, among other things. For example, the attachment devices 33 may include slots 33 for receiving a screw, a screw to mate with a slot on another ultrasound machine component, adhesive, hook and loop fasteners, or any suitable attachment device.

The side panel 30 and probe holder apparatuses 100 illustrated in FIG. 6 share various characteristics with the side panels 30 and probe holder apparatuses 100 illustrated in FIGS. 1-5 as described above.

Figure 7:
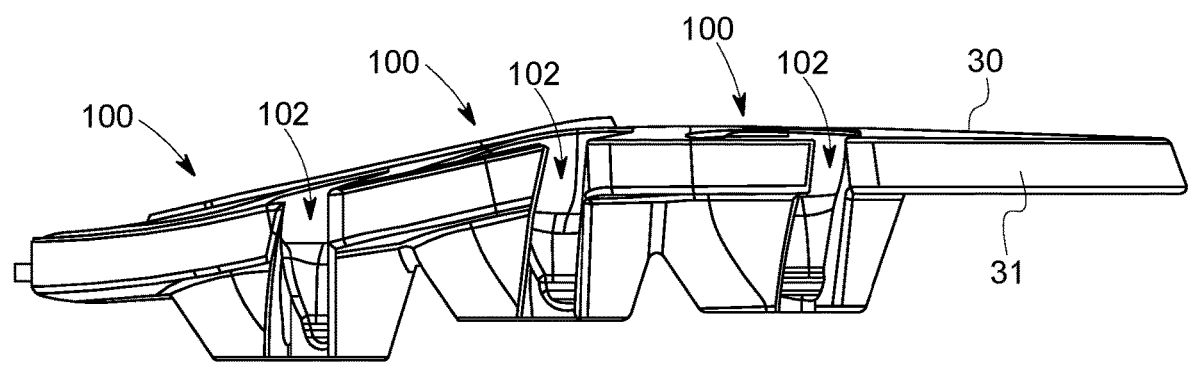
FIG. 7 illustrates an outer side elevation view of an exemplary panel of an ultrasound machine having ultrasound system probe holder apparatuses that include at least one cable guide, in accordance with various embodiments.
Figure 8:
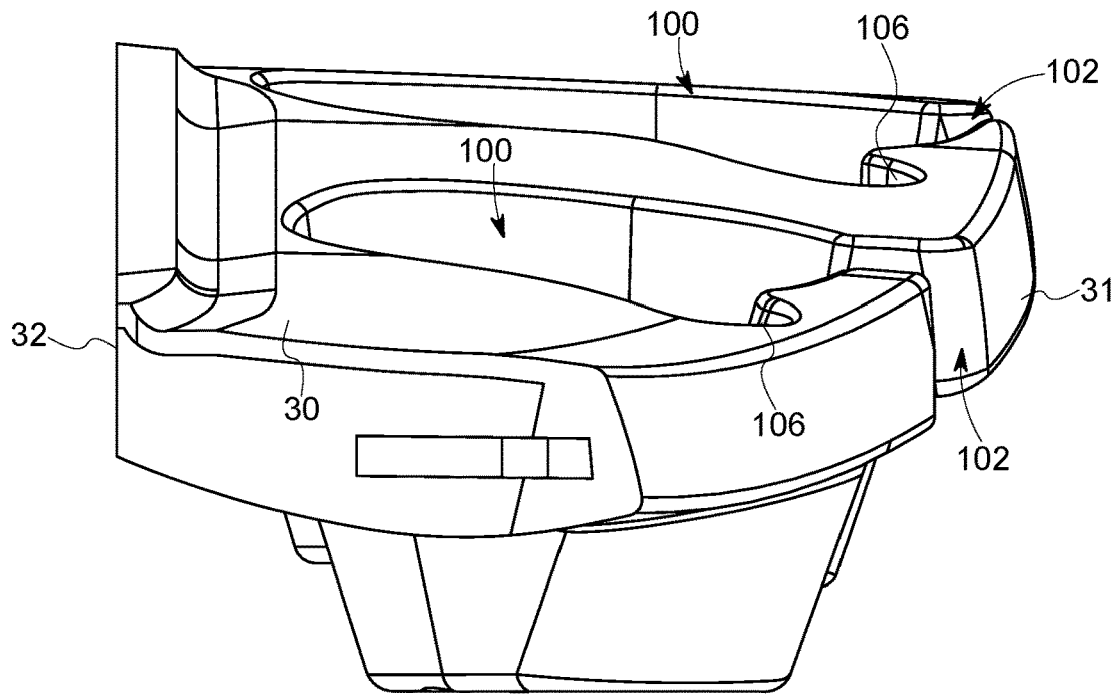
FIG. 8 illustrates a front perspective view of an exemplary panel of an ultrasound machine having ultrasound system probe holder apparatuses that include at least one cable guide, in accordance with various embodiments.
Figure 9:
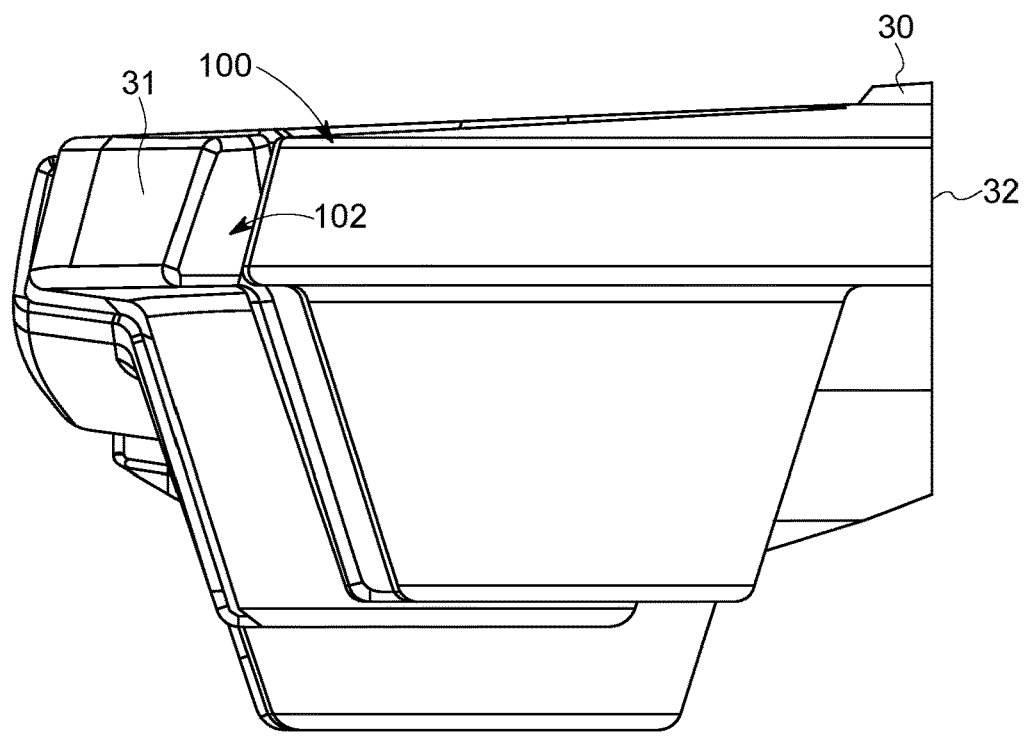
FIG. 9 illustrates a rear perspective view of an exemplary panel of an ultrasound machine having ultrasound system probe holder apparatuses that include at least one cable guide, in accordance with various embodiments.

FIG. 7 illustrates an outer side elevation view of an exemplary panel 30 of an ultrasound machine 1 having ultrasound system probe holder apparatuses 100 that include at least one cable guide 106, in accordance with various embodiments. FIG. 8 illustrates a front perspective view of an exemplary panel 30 of an ultrasound machine 1 having ultrasound system probe holder apparatuses 100 that include at least one cable guide 106, in accordance with various embodiments. FIG. 9 illustrates a rear perspective view of an exemplary panel 30 of an ultrasound machine 1 having ultrasound system probe holder apparatuses 100 that include at least one cable guide 106, in accordance with various embodiments. Referring to FIGS. 7-9, the panel 30 comprises outer 31 and inner edges 32 with one or more probe holder apparatuses 100 formed between the edges 31, 32. The inner edge 32 may be secured to other components of an ultrasound machine 1 and/or form a portion of a portable cart of the ultrasound machine 1, among other things. The outer edge 31 may define slots 102 of the one or more probe holder apparatuses 100 for providing access by an ultrasound probe 200 to the probe holder apparatuses 100. The one or more probe holder apparatuses 100 may comprise the slot 102 and a cable guide 106. The slot 102 may extend from a center of the probe holder apparatus 100 through a rear, outer corner and through the outer edge 31 of the panel 30. The slot 102 provides access by a probe cord 206 of an ultrasound probe into the probe holder apparatus 100. The cable guide 106 may be a generally semi-circular surface (e.g., U-shaped) protruding from a front, outer corner of the probe holder apparatus 100. The cable guide 106 may incline from within the probe holder apparatus 100 outward into the protruding portion of the cable guide 106. The cable guide 106 may be configured to slidably receive a probe cable 206 when the ultrasound probe 200 is pulled away from the probe holder apparatus 100.

The side panel 30 and probe holder apparatuses 100 illustrated in FIGS. 7-9 share various characteristics with the side panels 30 and probe holder apparatuses 100 illustrated in FIGS. 1-6 as described above.

Although the panel 30 is described as being a component of an ultrasound machine 1, unless so claimed, the panel 30 need not be part of the ultrasound machine 1 and may be any suitable structure having at least one integrated probe holder apparatus 100. The panel 30 may be a portable structure configured to be positioned in the vicinity of an ultrasound system and/or an ultrasound system may be configured to be positioned in the vicinity of the panel 30.

Aspects of the present disclosure provide a panel 30 comprising an inner edge 32, an outer edge 31 opposite the inner edge 32, and a probe holder apparatus 100 formed in the panel 30 between the inner edge 32 and the outer edge 31. The probe holder apparatus 100 may have a generally rectangular shape comprising a front outer corner, a rear outer corner, a front inner corner, and a rear inner corner. The probe holder apparatus 100 may comprise a slot 102 extending from a center of the probe holder apparatus 100 through the outer edge 31 of the panel 30. The probe holder apparatus 100 may comprise at least one surface 110 within the probe holder apparatus 100 configured to receive a body 204 of an ultrasound probe 200. The at least one surface 110 may have a diameter. The probe holder apparatus 100 may comprise a cable guide 106 comprising an inclined surface protruding from the front outer corner of the probe holder apparatus 100.

In a representative embodiment, the slot 102 may extend at an angle from the center of the probe holder apparatus 100 through the rear outer corner of the probe holder apparatus 100 and through the outer edge 32 of the panel 30. In an exemplary embodiment, the front inner corner and the rear inner corner are rounded corners. In various embodiments, the at least one surface 110 is a plurality of tiered surfaces 112, 114, 116 each having a different diameter. In certain embodiments, each of the plurality of tiered surfaces 112, 114, 116 is non-continuous. In a representative embodiment, the plurality of tiered surfaces 112, 114, 116 may comprise a first surface 112 having a first diameter, a second surface 114 positioned below the first surface 112 and having a second diameter, and a third surface 116 positioned below the second surface 114 and having a third diameter. The first diameter may be greater than the second diameter and the second diameter may be greater than the third diameter. In an exemplary embodiment, the cable guide 106 is generally semi-circular. In various embodiments, the probe holder apparatus 100 may comprise a notched opening 104 extending between the cable guide 106 and the slot 102. In certain embodiments, the notched opening 104 is generally L-shaped and contiguous with the slot 102. In a representative embodiment, the panel 30 is a side panel of an ultrasound machine 1.

Various embodiments provide an ultrasound machine 1 that may comprise a display system 10, a control panel 20, an ultrasound probe 200, and at least one panel 30. The display system 10 may be configured to present an ultrasound image. The control panel 20 may comprise a plurality of user input devices 22, 24 configured to receive a user directive. The ultrasound probe 200 may comprise a transducer head 202, a probe body 204 attached to the transducer head 202, and a probe cord 206 extending from the probe body 204. The transducer head 202 may be configured to transmit and receive ultrasound signals. The at least one panel 30 may comprise an inner edge 32 facing the control panel 20, an outer edge 31 opposite the inner edge 32, and a probe holder apparatus 100 formed in the at least one panel 30 between the inner edge 32 and the outer edge 31. The probe holder apparatus 100 may have a generally rectangular shape that may comprise a front outer corner, a rear outer corner, a front inner corner, and a rear inner corner. The probe holder apparatus 100 may comprise a slot 102, at least one surface 110 within the probe holder apparatus 100, and a cable guide 106. The slot 102 may extend from a center of the probe holder apparatus 100 through the outer edge 31 of the at least one panel 30. The at least one surface 110 may be configured to receive the probe body 204 of the ultrasound probe 200. The at least one surface 110 may have a diameter. The cable guide 106 may comprise an inclined surface protruding from the front outer corner of the probe holder apparatus 100.

In an exemplary embodiment, the slot 102 of the probe holder apparatus 100 may extend at an angle from the center of the probe holder apparatus 100 through the rear outer corner of the probe holder apparatus and through the outer edge 31 of the at least one panel 30. In various embodiments, the at least one surface 110 of the probe holder apparatus 100 may be a plurality of tiered surfaces 112, 114, 116 each having a different diameter. In certain embodiments, each of the plurality of tiered surfaces 112, 114, 116 may be non-continuous. In a representative embodiment, the probe holder apparatus 100 may comprise a notched opening 104 extending between the cable guide 106 and the slot 102. In an exemplary embodiment, the notched opening 104 may be generally L-shaped and contiguous with the slot 102. In various embodiments, the cable guide 106 may be generally semi-circular. The cable guide 106 may be configured to slidably receive the probe cord 206 of the ultrasound probe 200 when the ultrasound probe 200 is pulled away from the probe holder apparatus 100. In certain embodiments, the at least one panel 30 may comprise two panels 30 positioned at opposite sides of the control panel 20. In a representative embodiment, the at least one panel 30 may comprise a plurality of the probe holder apparatus 100. Each of the plurality of the probe holder apparatus 100 may be formed in the at least one panel 30 between the inner edge 32 and the outer edge 31. In an exemplary embodiment, the inner edge 32 of the at least one panel may comprise an attachment device 33 configured to attach the at least one panel 30 to another component of the ultrasound machine 1.

As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, a component is "operable" or "configured" to perform a function whenever the component comprises the necessary structure to perform the function, regardless of whether performance of the function is disabled, or not enabled, by some user-configurable setting.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A panel comprising:
an inner edge;
an outer edge opposite the inner edge; and
a probe holder apparatus formed in the panel between the inner edge and the outer edge, the probe holder apparatus having a generally rectangular shape comprising a front outer corner having a bump-out projection, a rear outer corner, a front inner corner, and a rear inner corner, the probe holder apparatus comprising:
a slot extending at an angle from a center of the probe holder apparatus through the rear outer corner of the probe holder apparatus and through the outer edge of the panel;
at least one surface within the probe holder apparatus configured to receive a body of an ultrasound probe, the at least one surface having a diameter; and
a cable guide comprising an inclined surface extending from the bump-out projection at the front outer corner within the probe holder apparatus downward and inward toward the center of the probe holder apparatus,
wherein the panel is a lateral side panel of an ultrasound machine.

2. The panel of claim 1, wherein the front inner corner and the rear inner corner are rounded corners.

3. The panel of claim 1, wherein the at least one surface is a plurality of tiered surfaces each having a different diameter.

4. The panel of claim 3, wherein each of the plurality of tiered surfaces is non-continuous.

5. The panel of claim 3, wherein the plurality of tiered surfaces comprises a first surface having a first diameter, a second surface positioned below the first surface and having a second diameter, and a third surface positioned below the second surface and having a third diameter, wherein the first diameter is greater than the second diameter and the second diameter is greater than the third diameter.

6. The panel of claim 1, wherein the cable guide is generally semi-circular.

7. The panel of claim 1, wherein the probe holder apparatus comprises a notched opening extending between the cable guide and the slot.

8. The panel of claim 7, wherein the notched opening is generally L-shaped and contiguous with the slot.

9. An ultrasound machine comprising:
a display system configured to present an ultrasound image;
a control panel comprising a plurality of user input devices configured to receive a user directive;
an ultrasound probe comprising:
a transducer head configured to transmit and receive ultrasound signals;
a probe body attached to the transducer head; and
a probe cord extending from the probe body; and
at least one lateral side panel comprising:
an inner edge facing the control panel;
an outer edge opposite the inner edge; and
a probe holder apparatus formed in the at least one lateral side panel between the inner edge and the outer edge, the probe holder apparatus having a generally rectangular shape comprising a front outer corner having a bump-out projection, a rear outer corner, a front inner corner, and a rear inner corner, the probe holder apparatus comprising:
a slot extending at an angle from a center of the probe holder apparatus through the rear outer corner of the probe holder apparatus and through the outer edge of the at least one lateral side panel;
at least one surface within the probe holder apparatus configured to receive the probe body of the ultrasound probe, the at least one surface having a diameter; and
a cable guide comprising an inclined surface extending from the bump-out projection at the front outer corner within the probe holder apparatus downward and inward toward the center of the probe holder apparatus.

10. The ultrasound machine of claim 9, wherein the at least one surface of the probe holder apparatus is a plurality of tiered surfaces each having a different diameter.

11. The ultrasound machine of claim 10, wherein each of the plurality of tiered surfaces is non-continuous.

12. The ultrasound machine of claim 9, wherein the probe holder apparatus comprises a notched opening extending between the cable guide and the slot.

13. The ultrasound machine of claim 12, wherein the notched opening is generally L-shaped and contiguous with the slot.

14. The ultrasound machine of claim 9, wherein the cable guide is generally semi-circular, the cable guide configured to slidably receive the probe cord of the ultrasound probe when the ultrasound probe is pulled away from the probe holder apparatus.

15. The ultrasound machine of claim 9, wherein the at least one lateral side panel comprises two lateral side panels positioned at opposite lateral sides of the control panel.

16. The ultrasound machine of claim 9, wherein the at least one lateral side panel comprises a plurality of the probe holder apparatus, each of the plurality of the probe holder apparatus formed in the at least one lateral side panel between the inner edge and the outer edge.

17. The ultrasound machine of claim 9, wherein the inner edge of the at least one lateral side panel comprises an attachment device configured to attach the at least one lateral side panel to another component of the ultrasound machine.

* * * * *